United States Patent [19]

Heimansohn

[11] 4,014,095

[45] Mar. 29, 1977

[54] RESILIENT ARTIFICIAL DENTURE TOOTH

[75] Inventor: Henry C. Heimansohn, Danville, Ind.

[73] Assignee: Indiana University Foundation, Bloomington, Ind.

[22] Filed: Oct. 8, 1975

[21] Appl. No.: 620,251

Related U.S. Application Data

[63] Continuation-in-part of Ser. No. 532,513, Dec. 13, 1974, Pat. No. 3,958,334.

[52] U.S. Cl. .................................................. 32/8
[51] Int. Cl.² ........................................ A61C 13/00
[58] Field of Search ................................. 32/2, 8

[56] References Cited

UNITED STATES PATENTS

| | | | |
|---|---|---|---|
| 2,380,468 | 7/1945 | Saffir | 32/8 |
| 2,880,508 | 4/1959 | Lester et al. | 32/2 |
| 3,722,094 | 3/1973 | Rivoir | 32/2 |

*Primary Examiner*—Robert Peshock
*Attorney, Agent, or Firm*—Jenkins, Hanley & Coffey

[57] ABSTRACT

An artificial tooth for use in a denture comprising a base portion, an occlusal portion, and an intermediate portion sandwiched between and secured to the base portion and occlusal portion, the intermediate portion being resilient to permit the occlusal portion yieldably to move relative to the base portion. The intermediate portion is disposed generally at equal vertical distances from the occlusal surface of the occlusal portion and the ridge lap surface of the base portion. Two connecting members, spaced apart in the mesial-distal direction, are provided for limiting the movement of the occlusal portion relative to the base position. Such members are rigidly connected to the occlusal portion and loosely pivotally connected to the base portion. The loose pivotal connection permits the occlusal portion to move from its normal portion toward the base portion even by tipping movement. The tooth may also include vertically extending tabs or projections connected to the occlusal portion or the base portion or both to limit the movement of the occlusal portion. The projections may be so situated between the occlusal and base portions to prevent excessive tilting of the occlusal portion, a pinching of the resilient portion and rotation of the occlusal portion with respect to the base portion.

17 Claims, 17 Drawing Figures

RESILIENT ARTIFICIAL DENTURE TOOTH

This is a continuation-in-part of my prior patent application Ser. No. 532,513, filed Dec. 13, 1974 and now Pat. No. 3,958,334 issued May 25, 1976 and entitled Resilient Artificial Denture Tooth.

The present invention relates to dentures and particularly to the provision of a resilient artificial tooth for use in dentures.

It will be appreciated that the human bite is not merely opening and closing like a gate hinge, but, in addition, when chewing, has a complicated lateral and protrusive movement with the mandibular teeth moving on a spherical pattern having a radius of about four inches with the center of the sphere being above the mandibular teeth. The movements are different for each individual and are regulated by muscles of mastication and the temporomandibular joints. My present invention provides an artificial tooth for a denture, the occlusal portion of that tooth having resilient resisted movement relative to the base portion. In a set of dentures, including upper and lower dentures, I could provide eight resilient lower posterior teeth (four on each side) that would have vertical individual movements of occlusal (biting) surfaces concurrently with tipping of the occlusal surfaces.

My preferred artificial tooth comprises a base portion, an occlusal portion, and an intermediate portion sandwiched between and secured to the base portion and occlusal portion, the intermediate portion being resilient to permit the occlusal portion yieldably to move relative to the base portion. The occlusal portion provides, at its upper end, an occlusal surface and the base portion provides, at its lower end, a ridge lap surface. Preferably, the intermediate portion is disposed generally at equal vertical distances from the occlusal surface and the ridge lap surface. The terms "generally at equal vertical distances" is intended to encompass a considerable latitude. Particularly, I prefer that the intermediate resilient portion be about onehalf way up the height of the tooth, well below the occlusal surface and well above the ridge lap surface. The intermediate portion may have different thicknesses such as 1 mm, 1.5 mm, 2 mm, 2.5 mm, etc., up to, for instance, 4 or 5 mm if a patient has very resorbed ridges.

By placing the intermediate region at generally the vertical center of the tooth, I provide for an optimal resiliently resisted movement of the occlusal portion. The horizontally extending resilient intermediate section of each lower posterior tooth reduces very significantly the rocking of the base portion of the denture on either side, right or left. The occlusal portion will compress toward the base portion or against the resilient intermediate portion or tip in all directions such as mesial, distal, buccal, lingual or between these positions as dictated by the occlusion of the opposing dental arch. Thus, each tooth will automatically respond to changes in occlusion of the opposite dental arch. This results in balanced occlusion, less alveolar bone loss and greater comfort. I presently believe that the thickness of the resilient intermediate portion should be a minimum of 1 mm while the maximum thickness may range up to, for instance, 4 or 5 mm.

The compressive-resilient tooth of my invention allows individual teeth automatically to adjust in vertical and tipping movements to the patient's jaw movements and condyle inclination in occlusion, thus decreasing the need for extensive preconstruction registrations which are conventionally used in constructing dentures with conventional artificial teeth.

With my resilient teeth used as the posterior teeth of both sides for the lower denture, if a bolus of food is placed on the right working side, for example, between compressive resilient teeth and the teeth made to occlude, then the teeth on the right side will be depressed and the balancing side or left side will remain in contact. Thus, the denture will be balanced continuously in mastication.

By having the two separate anchor wires or the two separate legs of the U-shaped anchor wire, I prevent rotation of the occlusal portion relative to the base, which rotation would result in dislodging of the occlusal portion.

My anchor wire retention system is importantly internal to the tooth and not exposed to the mouth.

Further, importantly, my connecting means or anchor wire means serve to prevent occlusal portion from moving from its normal unloaded position away from the base portion to the extent that the resilient intermediate portion would be broken. My connecting means or anchor wire means permit the occlusal portion to move from its normal unloaded position toward the base portion to compress the resilient material of the intermediate portion.

My resilient tooth may also include a plurality of vertically extending tabs or projections extending from the adjacent surfaces of the base or occlusal portions. Such projections prevent excessive rotation of the occlusal portion with respect to the base, prevent excessive tilting and compression of the occlusal portion relative to the base, and protect the resilient intermediate portion. The projections, which may be interengaged to prevent relative rotation, are cut by the dentist after the denture is completed selectively to adjust the permitted movement of the occlusal portion.

Figure 1:
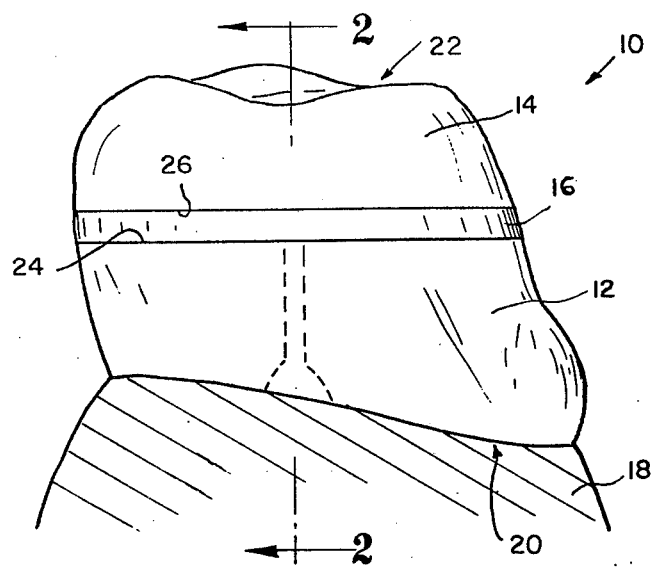
FIG. 1 is a fragmentary view of a portion of a denture showing my resiliently compressible tooth mounted thereon.
Figure 2:
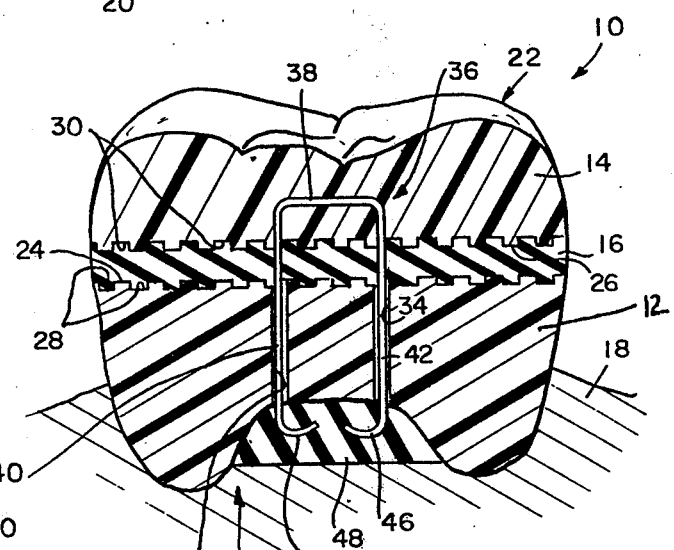
FIG. 2 is a fragmentary sectional view taken generally along line 2—2 in FIG. 1.

Referring now to the drawings, and particularly to FIGS. 1 and 2, it will be seen that I have illustrated my artificial tooth 10 as comprising a base portion 12, an occlusal portion 14, and an intermediate resilient portion 16. The base portion 12 is mounted upon a denture base, a portion of which is indicated at 18. The reference numeral 20 indicates the ridge lap surface of the tooth while the reference numeral 22 indicates the occlusal surface of the tooth.

The intermediate portion 16 is sandwiched between the upwardly facing surface 24 provided by the base 12 and the downwardly facing surface 26 or lower surface provided by the occlusal portion 14. These surfaces 24, 26, which are preferably generally congruently superposed, lie in horizontally extending planes as bonding surfaces. In some cases, as illustrated, the bonding surfaces may be provided with small cavities or cross ridges as desired, as indicated by the reference numerals 28, 30.

Two holes 32, 34 extend vertically through the base portion 12, the holes lying in a plane which is approximately the center mesial-distal section of the tooth. Means for connecting the occlusal portion 14 to the base portion 12 is indicated generally by the reference numeral 36, illustrative means including a generally U-shaped anchor wire having a base 38 which is rigidly secured to the occlusal portion 14 and vertically downwardly extending legs 40, 42 received, respectively, in the through holes 32, 34. The distal end portions 44, 46 of the legs 40, 42 are bent inwardly or toward each other as illustrated to restrain the anchor wire from moving vertically upwardly relative to the base portion 12. It will be seen that the ridge lap surface 20 provides a well into which the portions 44, 46 extend, which well may be filled with resilient material indicated at 48 which serves to prevent the base 18 material from entering the well during the processing of the dentures. Since the holes 32, 34 are larger in diameter than the wire legs 40, 42, some tipping movement or lateral movement of the occlusal portion 14 relative to the base portion 12 is permitted. Of course, the legs 40, 42 and the end portions 44, 46 can move downwardly relative to the base portion 12 to accommodate the compression of the resilient portion 16.

Figure 3:
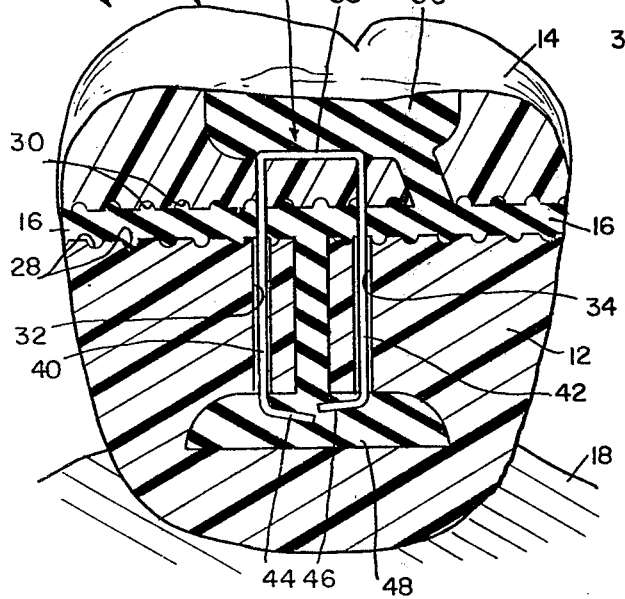
FIG. 3 is a fragmentary sectional view of another slightly different tooth in accordance with my present invention.

The embodiment of FIG. 3 indicated generally by the reference numeral 10', is very similar to the embodiment of FIGS. 1 and 2, like reference numerals representing like parts. The primary difference in the embodiment of FIG. 3 is the provision of a hollowed-out cavity 50 into which the resilient material is injected to cushion the upper or base portion 38. Thus, in the embodiment of FIG. 3, the anchor wire is not so rigidly attached to the occlusal portion 14.

I have said that the anchor wire 36 is rigidly secured to the occlusal portion 14 in FIGS. 1 and 2. This may be accomplished, for instance, by molding that occlusal portion with the wire extending into the mold. Any number of other techniques may be used rigidly to secure such an anchor wire or connector member to the occlusal portion.

Referring now to FIGS. 4–7, it will be seen that I have shown a resilient tooth indicated generally by the reference numeral 60, like reference numerals indicating like parts. One difference between the tooth 60 and the tooth 10 of FIGS. 1 and 2, is the manner in which the occlusal portion 14 is restrained from moving from its normal position away from the base portion 12. Instead of an inverted U-shaped anchor wire, there are two separate wires 40, 42 the upper ends of which are bent as indicated at 40a, 42a. Then, the distal ends of the through holes 32, 34 are enlarged as indicated at 32a, 34a to provide sockets 62, 64 in the base portion 12 for receiving the enlarged distal ends 66, 68 of the wires 40, 42. These enlarged opening 32a, 34a may preferably be plugged with a soft elastic material such as indicated at 70, 72 which prevents the hard acrylic base 18 material from flowing upwardly into the sockets 62, 64 to impede the movement of the enlarged distal ends 66, 68.

One advantage of my inventive resilient tooth is that a considerable amount of the occlusal surface 22 as well as the ridge lap surface 20 may be removed by grinding without, in any way, interfering with my mechanism for resiliently mounting the occlusal portion 14 on the base portion 12 and restraining the occlusal portion from moving away or tearing away from the base portion. The reference numerals 74, 76 indicate, respectively, the amount of occlusal surface 22 and ridge lap surface 20 which can be removed from the tooth 60. This feature applies also to the tooth 10, 10' of FIGS. 1, 2 and 3. Mass-produced teeth in accordance with my invention may be custom ground to fit a particular denture requirement.

Figure 4:
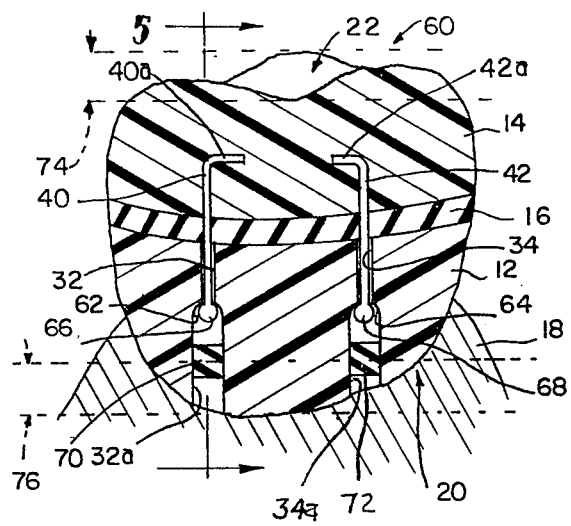
FIG. 4 is a fragmentary sectional view taken through the tooth along a vertical plane lying in the mesial-distal direction.

The sectional view of FIG. 4 is taken through a vertical plane extending centrally through the tooth in the mesial-distal direction. The two wires 40, 42 spaced apart in this plane serve to prevent the occlusal portion 14 from rotating about a vertical axis relative to the base portion 12, which rotation would be destructive to the intermediate resilient layer 16.

Figure 5:
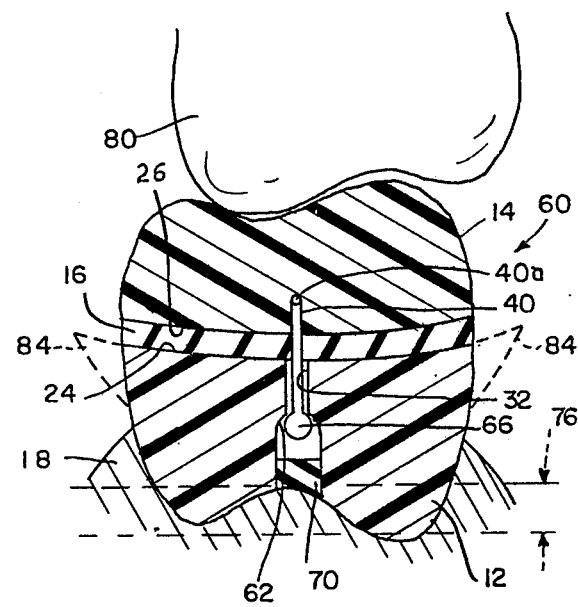
FIG. 5 is a fragmentary sectional view taken along the lines 5—5 in FIG. 4.
Figure 6:
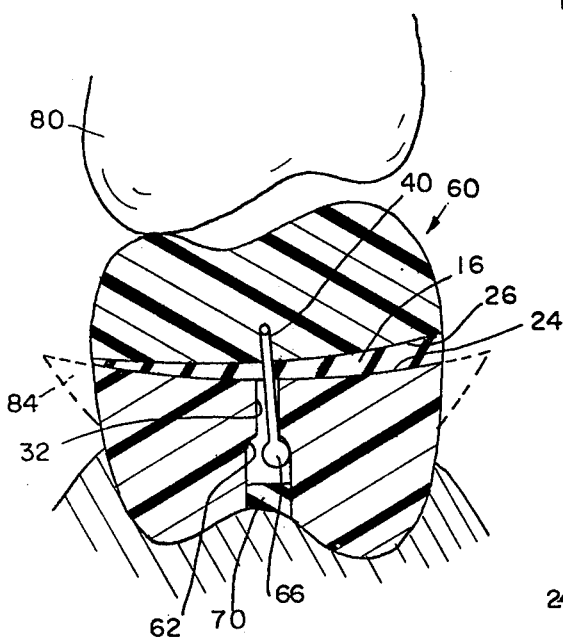
FIGS. 6 and 7 are sectional views similar to FIG. 5 but showing different tipping movement of the occlusal portion.
Figure 7:
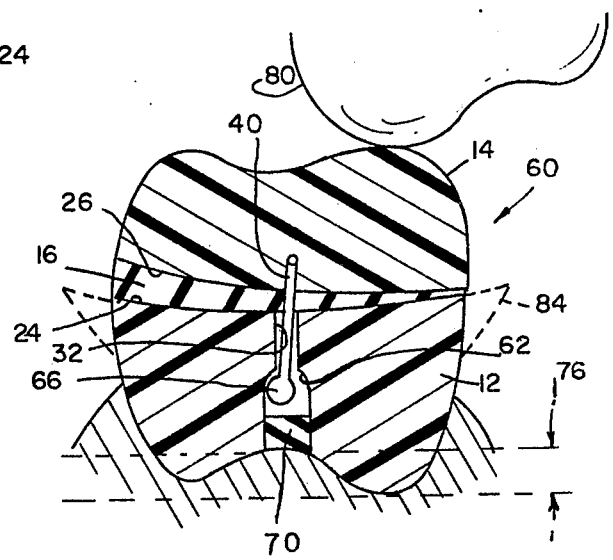

In the views 5, 6 and 7, I show an upper tooth 80 engaging the tooth 60, the views of FIGS. 5, 6 and 7 being taken in the buccal-lingual direction with the right-hand side of each view being the buccal or facial side and the left-hand side of each view being the lingual or tongue side. FIG. 5 shows the right side denture tooth 60 in occlusion with no pressure on the resilient portion 16. The retainer ball or enlarged end 66 is generally at the top of the socket 62. This position of the occlusal portion 14 represents its normal or unloaded position. It will be appreciated that the occlusal portion 14 cannot move vertically upwardly from the position of FIG. 5 because of the restraining feature of the enlarged end portion 66.

FIG. 6 shows a right lateral excursion of the mandible and lower denture with the occlusal portion 14 depressed and tipping to the lingual side. The retainer ball or enlarged end portion 66 depresses to the bottom of the socket 62 and is angulated in the over-sized hole 32. FIG. 7 shows a left lateral excursion of the mandible with the occlusal portion 14 depressed and tipping on the buccal side with the wire 40 angulated in the opposite direction relative to that shown in FIG. 6. The occlusal portion 14, therefore, can accommodate a considerable amount of excursion or grinding of the engaging occlusal surfaces of opposed teeth. The occlusal portion 14 can tip in any direction, i.e., from side to side in the buccal-lingual direction or from front to back in the mesial-distal direction.

I show laterally outwardly extending lugs or lips 84 in dashed lines on the base portion 12 of the tooth 60. These lugs 84 serve to position the base portion 12 in the dental plaster or stone of a split metal flask indicated at 86 in FIG. 8, the flask having an upper half 88 and a lower half 90. The plastic material from which the denture base 18 is made is mixed like putty and placed between the two halves 88, 90 of the flask with the parting line of the flask being indicated at 92. Then the flask is squeezed together. The lugs 84 will position themselves in the dental plaster in the flask to keep the base portion 12 from being forced against the occlusal portion 14 to place the intermediate layer 16 in compression during the squeezing process. After the denture is removed from the flask, the lugs 84 are removed by grinding and polishing operations.

Figure 9:
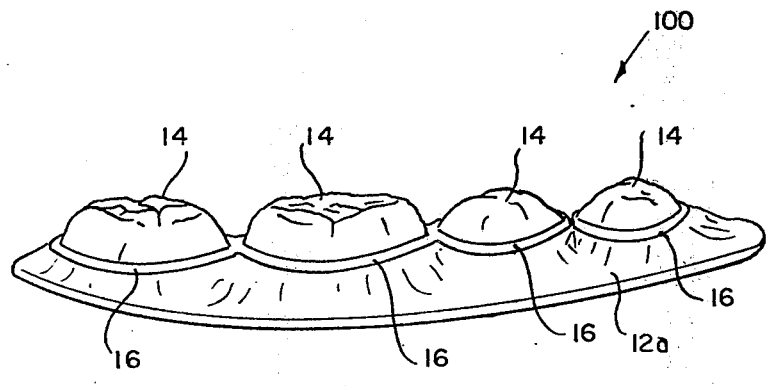
FIG. 9 is a perspective view showing a common base portion elongated in the mesial-distal direction with four occlusal portions resiliently mounted on the common base portion.

In the embodiment of FIG. 9, indicated generally at 100, four separate and individually yieldably movable occlusal portions 14 are mounted upon a common base portion 12a and resiliently supported thereon by intermediate portions 16. Each of the individual occlusal portions 14 in FIG. 9 are restrained from moving away from the base portion 12a by anchor wires such as indicated at 40, 42 in other embodiments. The entire base portion 12a, therefore, would be mounted upon a denture base 18 as an assembly.

Figure 10:
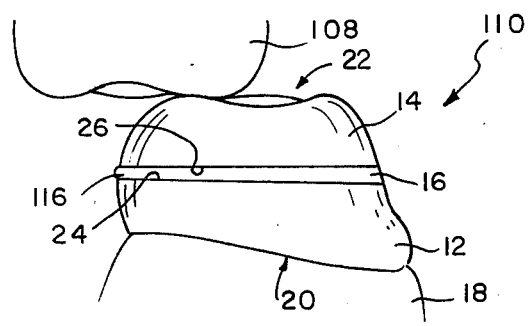
FIG. 10 is a view, from either the mesial or distal direction, of a portion of a prior art denture having a strip of resilient material extending therethrough.

In FIG. 10, I have illustrated a prior art artificial tooth 110, again comprising a base portion 12, an occlusal portion 14, and an intermediate resilient portion 16. The base portion 12 is mounted upon a denture base, a portion of which is indicated at 18. The occlusal surface of the tooth is indicated by the reference numeral 22 and the ridge lap surface of the tooth is indicated by reference numeral 20. As before, the resilient intermediate portion 16 is sandwiched between an upwardly facing surface 24 provided by base 12 and a downwardly facing surface 26 provided by occlusal portion 14.

An upper tooth 108 engages the occlusal surface 22 of tooth 110, exerting pressure on either the buccal or lingual side thereof and causing the occlusal portion 14 of tooth 110 to tilt in response to the pressure exerted. Extensive compression of resilient layer 16 caused by this pressure results in a bulging or pinching of the resilient layer 16 on either the buccal or lingual side of tooth 110 as indicated at reference numeral 116. It is generally desirable to limit this bulging of resilient layer 16, since excessive bulging of the resilient layer 16 may cause damage thereto.

In the embodiments of FIGS. 11–14, the tilting of the occlusal portion 14 of such a tooth 110 is limited, thereby limiting the resultant bulging of the resilient layer 16 in either the buccal or lingual direction. It is to be understood that the concepts embodied in the teeth of FIGS. 11–14 may be applied equally as effectively to limit the tilting of the occlusal portion 14 of such a tooth 110 in the mesial-distal direction.

Figure 11:
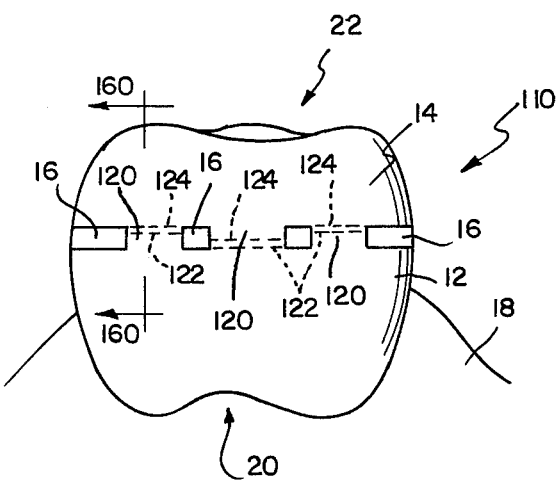
FIG. 11 is a view, from either the buccal or lingual side, of a tooth constructed in accordance with an embodiment of the present invention before activation of the strip of resilient material.
Figure 12:
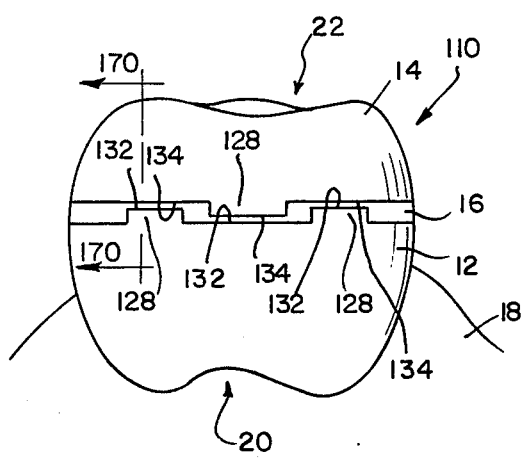
FIG. 12 is a view, from either the buccal or lingual side, of the tooth of FIG. 11 after activation of the strip of resilient material.

In the embodiment of FIGS. 11–12, the base portion 12 and occlusal portion 14 are joined along their buccal and lingual sides by a plurality of vertically extending projections or tabs 120, the tabs 120 extending at the tooth 110 outer perimetral surface from the upper extent of base 12 to the lower extent of occlusal portion 14.

Each of tabs 120 is of limited thickness in the buccal-lingual direction to provide for relative ease of cutting the tabs between dashed lines 122 and 124 of the base portion 12 and occlusal portion 14, respectively. This cutting apart of the base 12 and occlusal portion 14 may be accomplished after the denture is completed and even after the denture is tried by the patient. As can be appreciated, this cutting apart of base 12 and occlusal portion 14 activates the resilient layer 16, i.e., allows depression of occlusal portion 14 to compress resilient layer 16. If a patient needs more movement of the occlusal portion 14 after trying the denture, the distance between the cutting lines can be increased selectively.

As best illustrated in FIG. 12, the separating of base 12 and occlusal portion 14 of the tooth 110 establishes on the buccal and lingual sides of tooth 110 a plurality of engaging projecting tabs 128 and establishes between the distal ends of projecting tabs 128 and the opposite surfaces of the base portion 12 or occlusal portion 14 two substantially parallel planes 132, 134. It is the separation of these planes 132, 134 as well as the relative location and separation of the projecting tabs 128 along the buccal and lingual sides of the tooth 110 which determine the extent to which resilient layer 16 can be compressed in the buccal-lingual directions as well as in the mesial-distal directions. Separation of alternating ones of connecting tabs 120 at opposite ends establishes first engaging tabs 128 extending from occlusal portion 14 toward base portion 12 and second engaging tabs 128 extending from base portion 12 toward occlusal portion 14.

Figure 15:
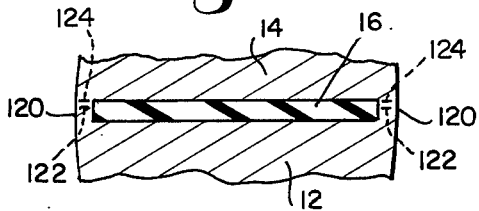
FIG. 15 is a fragmentary sectional view of the tooth of FIG. 11 taken along section lines 160—160 thereof.
Figure 16:
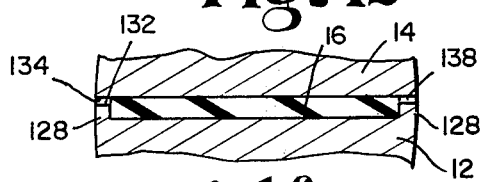
FIG. 16 is a fragmentary sectional view of the tooth of FIG. 12 taken along section lines 170—170 thereof.

FIG. 15 is a fragmentary sectional view of the tooth of FIGS. 11–12 before tabs 120 of tooth 110 are cut to free occlusal portion 14 for movement relative to base portion 12. As shown in FIG. 16, after separation of tabs 120 between dotted lines 122, 124, resilient intermediate portion 16 is activated for compression. It can be seen from FIG. 16 that after tabs 120 are cut to form engaging projecting tabs 128, grooves 138 result in the outer perimeter of tooth 110 between the generally parallel surfaces 132, 134. Grooves 138 can be filled with resilient material like or similar to that used in resilient intermediate portion 16 of tooth 110 to prevent food particles from accumulating in grooves 138.

Figure 13:
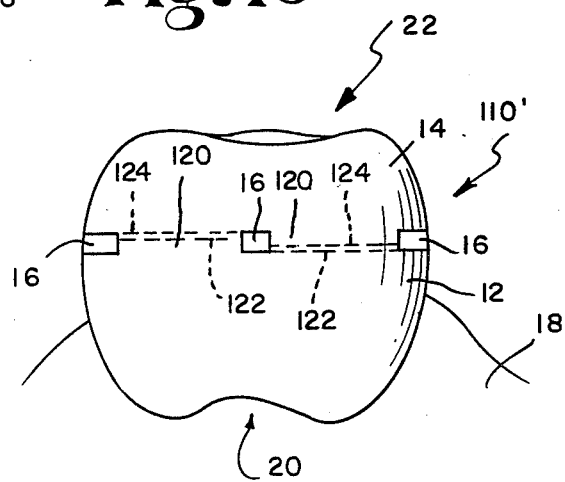
FIG. 13 is a view, from either the buccal or lingual side, of a tooth constructed in accordance with an embodiment of the present invention before activation of the strip of resilient material.
Figure 14:
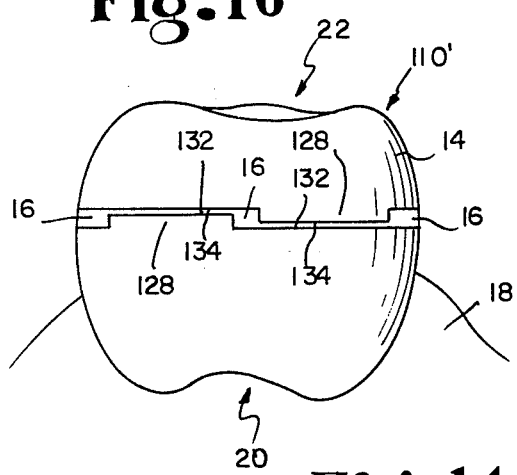
FIG. 14 is a view, from either the buccal or lingual side, of the tooth of FIG. 13 after activation of the strip of resilient material.

FIGS. 13–14 illustrate an alternative arrangement for tabs 120. As in the embodiment of FIGS. 11–12, the tabs 120 of FIG. 13 may be cut along dotted lines 122, 124 to produce engaging projecting tabs 128 along the buccal and lingual sides of tooth 110'. See FIG. 14.

As can be appreciated from FIGS. 11–14, the projecting tabs 128 prevent excessive compression of resilient layer 16, excessive tilting of the occlusal portion 14 of each of teeth 110, 110', and relative rotation of occlusal portion 14 with respect to the base 12 of each of teeth 110, 110'. Additionally, tabs 128 aid in retaining the resilient material between occlusal portion 14 and base 12.

It is also understood that in mass-produced teeth made in accordance with the invention of FIGS. 11–14, when there are to be engaging tabs 128 on either the buccal or lingual side, or both, of tooth 110, 110', only one of the tabs 128 need be manufactured as a tab 120 connecting base 12 to occlusal portion 14. That is, only one of tabs 128 need bridge the entire gap between occlusal portion 14 and base 12. In such a situation, it would only be necessary to cut between the dotted lines 122, 124 of one of tabs 120 of the teeth of FIGS. 11–14, to separate the base 12 from the occlusal portion 14 and activate the resilient layer 16.

Figure 17:
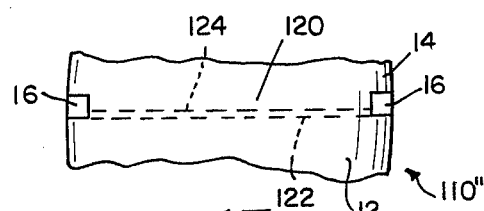
FIG. 17 is a fragmentary view, from either the buccal or lingual side, of a tooth constructed in accordance with the invention.

Instead of having the engaging projecting tabs 128 resulting from activation of the resilient intermediate portions 16 of the teeth of FIGS. 11–16, tooth 110" of FIG. 17 has only a single tab 120 on its buccal or lingual side, or both. Of course, when tab 120 of tooth 110" is cut between dotted lines 122, 124, a single projecting tab will result. This single projecting tab will aid in retaining and protecting the perimetral surface of resilient portion 16 between occlusal portion 14 and base 12. In addition, since rotation of occlusal portion 14 of tooth 110" relative to base portion 12 would require some compression of resilient portion 16, the single tab on the buccal and lingual sides of tooth 110" will help prevent rotation of occlusal portion 14 of tooth 110" relative to base 12.

Figure 8:
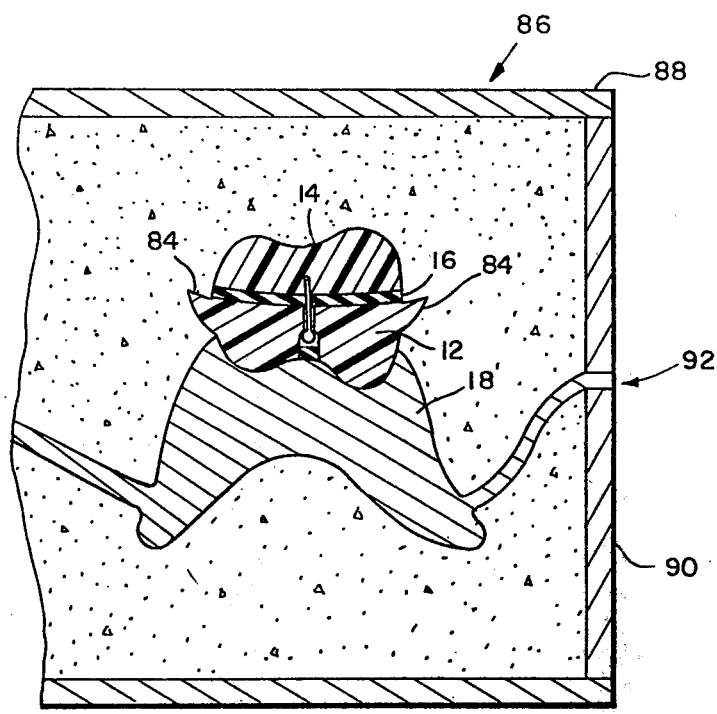
FIG. 8 is a fragmentary sectional view showing my tooth in a flask with lugs on the base portion of the tooth positioning the tooth in the dental plaster.

One of the primary advantages of the vertically extending tabs of FIGS. 11 to 17 is that the occlusal portion 14 is prevented from moving relative to the base portion 12 during processing of the denture in the flask 86 in FIG. 8. The occlusal portion 14 can move only after the tabs 120 are cut and then only by the selected depth of the cut.

It will be appreciated that the vertical tabs 120 may preferably be provided on resilient teeth which also include connecting means 36, i.e., the two spaced apart connecting members 40, 42 discussed hereinabove.

It will further be appreciated that the connecting tabs 120 between the occlusal portion 14 and base portion 12 may be disposed externally to the perimetral surfaces of the tooth so that, after the denture is completed, the tabs may be cut or ground away completely. In such a case, the tabs would be useful for rigidly positioning the occlusal portion during processing of the denture.

I have shown the resilient teeth of my present invention on the lower posterior sides of dentures. It will be appreciated that my resilient teeth may be placed upon upper denture plates as well as lower plates and even on partial denture plates.

I claim as my invention:

1. An artificial tooth for use in a denture, said tooth comprising a base portion, an occlusal portion and an intermediate portion, said base portion and occlusal portion each providing surfaces for securing said intermediate portion in sandwiched relation therebetween, said intermediate portion being resilient to permit said occlusal portion to move yieldably relative to said base portion, and a plurality of tabs for limiting movement of said occlusal portion relative to said base portion, said tabs projecting from at least one of said surfaces toward the other of said surfaces about the outer perimeter of one of said occlusal and base portions.

2. An artificial tooth according to claim 1 wherein said plurality of tabs comprises at least two engaging tabs, one of which projects from each of said surfaces toward the other of said surfaces, said oppositely directed tabs engaging to resist rotation of said occlusal portion relative to said base portion.

3. An artificial tooth according to claim 2 wherein each of said tabs extends a substantially greater distance about the perimeter of said tooth than its thickness in the buccal-lingual direction.

4. An artificial tooth according to claim 1 wherein said occlusal portion and said base portion provide at their ends remote from said intermediate portion an occlusal surface and a ridge lap surface, respectively, and said resilient intermediate portion lies approximately half-way between said ridge lap surface and said occlusal surface.

5. An artificial tooth according to claim 1 wherein said plurality of tabs comprises at least one tab on each of the buccal and lingual sides of said tooth.

6. An artificial tooth according to claim 1 wherein said plurality of tabs comprises at least a first tab projecting from said occlusal portion and a second tab projecting from said base portion of said tooth on each of the lingual and buccal sides thereof.

7. An artificial tooth for use in a denture, said tooth comprising a base portion, an occlusal portion and an intermediate portion, said occlusal and base portions each providing a surface for securing said intermediate portion in sandwiched relation between said base and occlusal portions, said intermediate portion being resilient to permit said occlusal portion to move yieldably relative to said base portion, and a plurality of tabs for limiting movement of said occlusal portion relative to said base portion, said tabs projecting from at least one of said surfaces part of the distance across the space between said surfaces toward the other of said surfaces to aid in retaining the intermediate portion between the surfaces, the tabs projecting across said space about the outer perimeter of the tooth.

8. An artificial tooth according to claim 7 wherein said plurality of tabs includes a first tab which projects from said occlusal portion surface toward said base portion and a second tab which projects from said base portion surface toward said occlusal portion.

9. An artificial tooth according to claim 7 wherein said plurality of tabs comprises at least one tab extending from each of said occlusal and base portions along the outer perimeter of said tooth on each of the buccal and lingual sides thereof for engaging a respective tab on the other of said surfaces.

10. In an artificial tooth for use in a denture, said tooth comprising a base portion, an occlusal portion and an intermediate layer sandwiched between and secured to said base portion and occlusal portion, said intermediate layer being resilient to permit said occlusal portion yieldably to move relative to said base portion, the improvement comprising a tab extending generally vertically from one of said portions toward the other of said portions about the outer periphery of said tooth, said tab having a distal end spaced apart from said other portion to serve as stop limiting such relative movement.

11. The improvement of claim 10 including a plurality of said tabs including first tabs extending downwardly from said occlusal portion and second tabs extending upwardly from said base portion, said first and second tabs engaging to resist rotation of said occlusal portion relative to said base portion.

12. An artificial tooth according to claim 11 wherein each of said tabs extends a substantially greater distance about the perimeter of said tooth than it does in the buccal-lingual direction of said tooth.

13. A method for making an artificial tooth having a base portion, an occlusal portion and an intermediate portion, each of said base and occlusal portions providing bonding surfaces for securing said intermediate portion in sandwiched relation between said base portion and said occlusal portion, said intermediate portion being resilient to permit said occlusal portion to move yieldably relative to said base portion, and tab means projecting between said occlusal portion and said base portion for limiting movement of said occlusal portion relative to said base portion, said tab means extending between said occlusal and base portions and about the perimeter of said tooth, said method comprising the steps of forming said occlusal portion and said base portion as one piece connected together by said tab means, bonding said resilient intermediate portion to said occlusal portion and said base portion, and trimming said tab means for allowing said occlusal portion to move yieldably relative to said base portion.

14. A method of making an artificial tooth comprising the steps of forming an occlusal portion and a base portion as one piece connected together by tab means, said tab means defining a space between said base portion and occlusal portion, filling said space with a resilient intermediate portion and bonding said resilient intermediate portion to said occlusal portion and said base portion, and disconnecting said tab means from one of said occlusal portion and base portion for allowing said occlusal portion to move yieldably relative to said base portion.

15. An artificial tooth for use in a denture, said tooth comprising a base portion, an occlusal portion, and an intermediate layer sandwiched between and secured to said base portion and occlusal portion, each said portion having a buccal side and lingual side, said intermediate layer being resilient to permit said occlusal portion yieldably to move relative to said base portion, in which the improvement comprises a vertically extending tab connected between said occlusal portion and said base portion on each side, said tab being rigid fixedly to position said occlusal portion to said base portion, whereby said occlusal portion is released for movement relative to said base portion by cutting said tab.

16. A method for making a denture including a plurality of teeth according to claim 15, said method including the steps of positioning said teeth in dental plaster in a flask, forming a denture base in a void in said plaster and upon which said teeth are mounted, and cutting said tabs to release said occlusal portions for movement relative to said base portions.

17. A method for constructing a denture having a plurality of resilient artificial teeth, each tooth having an occlusal portion and a base portion sandwiching therebetween a resilient layer, each tooth also having tab means rigidly positioning said occlusal portion on said base portion, said method comprising the steps of placing said teeth in a flask containing dental plaster formed to define a void for a denture base, said teeth being positioned in said plaster to protrude into said void, forming a denture base in said void and connected to said teeth, and cutting said tab means to release said occlusal portion for movement relative to said base portion.

* * * * *